United States Patent
Hurlstone et al.

(10) Patent No.: US 7,814,871 B2
(45) Date of Patent: *Oct. 19, 2010

(54) SELF-PRIMING PORTABLE DEVICE

(75) Inventors: Christopher John Hurlstone, Essex (GB); Robert Andrew Fry, Hertfordshire (GB); Stephen Philip Kirkwood, Bedfordshire (GB)

(73) Assignee: Team Holdings Limited (GB)

( * ) Notice: Subject to any disclaimer, the term of this patent is extended or adjusted under 35 U.S.C. 154(b) by 1653 days.

This patent is subject to a terminal disclaimer.

(21) Appl. No.: 10/492,254

(22) PCT Filed: Oct. 14, 2002

(86) PCT No.: PCT/GB02/04715

§ 371 (c)(1),
(2), (4) Date: Sep. 7, 2004

(87) PCT Pub. No.: WO03/033058

PCT Pub. Date: Apr. 24, 2003

(65) Prior Publication Data

US 2005/0000711 A1    Jan. 6, 2005

(30) Foreign Application Priority Data

Oct. 13, 2001 (GB) .................................. 01246586
Jul. 12, 2002 (GB) .................................. 02161636

(51) Int. Cl.
*F02B 71/00* (2006.01)

(52) U.S. Cl. ................. 123/46 SC; 123/46 H; 123/46 R
(58) Field of Classification Search ............. 123/46 SC, 123/46 H, 46 R; 604/141
See application file for complete search history.

(56) References Cited

U.S. PATENT DOCUMENTS 2,730,082 A * 1/1956 Aloyse .................... 123/46 SC (Continued)

FOREIGN PATENT DOCUMENTS

EP     0277480 A2    8/1988

(Continued)

*Primary Examiner*—Michael Cuff
*Assistant Examiner*—Hung Q Nguyen
(74) *Attorney, Agent, or Firm*—Barnes & Thornburg LLP

(57) ABSTRACT

A portable powered device such as a tool, comprising a housing within which is defined a combustion chamber (8) for combustion of a mixture of fuel and a combustion-supporting gas, which mixture is compressed so as to be subjected to a pressure in excess of the ambient atmospheric pressure prior to combustion, combustion of the fuel/combination-supporting gas mixture providing the power by which the device performs its intended task, and wherein the combustion and/or a further combustive event provides the power to compress a successive fuel/combination-supporting gas mixture, such that a successive cycle of operation of the device may be performed without requiring manual compression of a fuel-combustion-supporting gas mixture by the user.

8 Claims, 3 Drawing Sheets

U.S. PATENT DOCUMENTS

| | | | |
|---|---|---|---|
| 2,875,737 A * | 3/1959 | Ueckert | 123/41.56 |
| 3,610,214 A * | 10/1971 | Braun | 123/46 SC |
| 3,802,430 A | 4/1974 | Schwebel | |
| 3,967,771 A | 7/1976 | Smith | |
| 4,365,471 A * | 12/1982 | Adams | 60/39.76 |
| 4,415,110 A | 11/1983 | Hunter | |
| 4,534,500 A | 8/1985 | Jochum | |
| 4,665,868 A * | 5/1987 | Adams | 123/46 SC |
| 4,712,379 A * | 12/1987 | Adams et al. | 60/632 |
| 4,759,318 A * | 7/1988 | Adams | 123/46 SC |
| 5,197,646 A * | 3/1993 | Nikolich | 227/8 |
| 5,199,626 A * | 4/1993 | Terayama et al. | 227/10 |
| 7,281,502 B2 * | 10/2007 | Hurlstone et al. | 123/46 SC |

FOREIGN PATENT DOCUMENTS

| | | |
|---|---|---|
| EP | 0316468 A2 | 5/1989 |
| WO | WO 01/89612 A1 | 11/2001 |
| WO | WO 01/97880 A2 | 12/2001 |

* cited by examiner

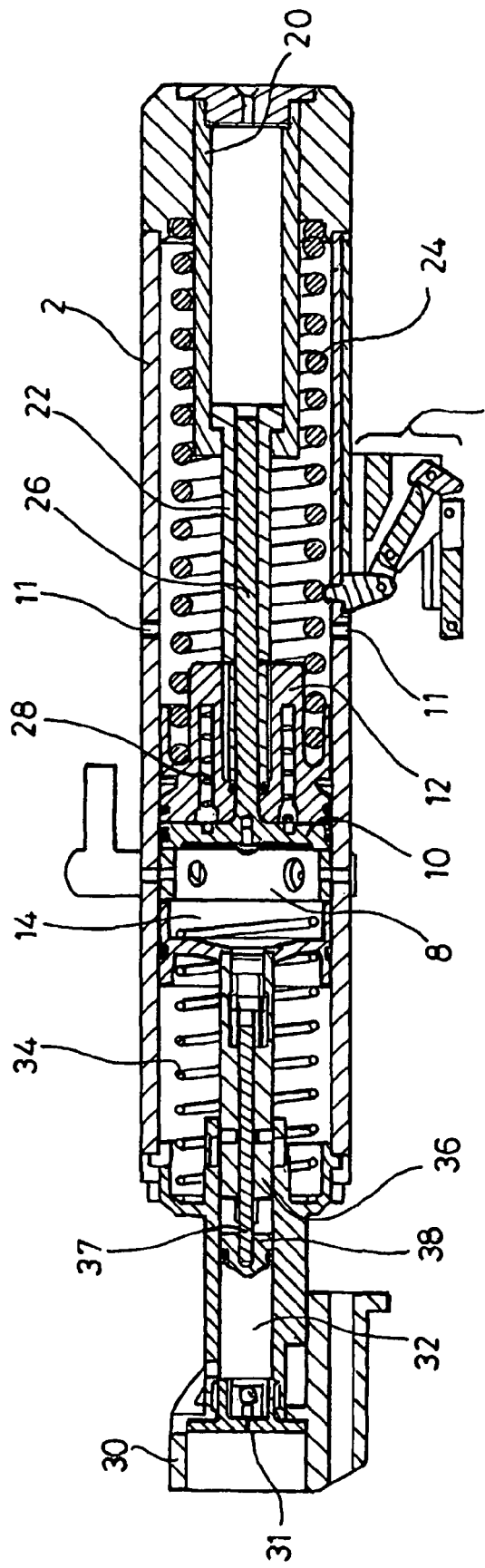
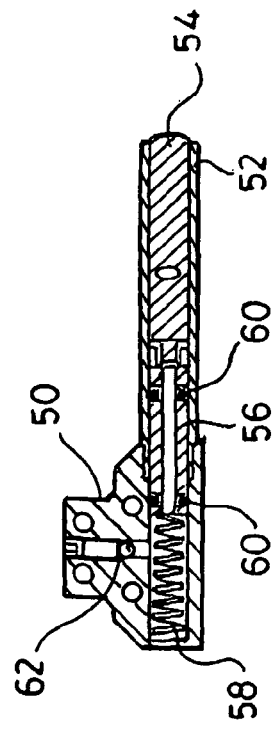
Fig. 2a
Fig. 2b

SELF-PRIMING PORTABLE DEVICE

FIELD OF THE INVENTION

The present invention relates to a self-priming portable device including, but not limited to, a self-priming portable injection device, and a method of making the device. The device of the invention includes an internal combustion engine as a power source.

BACKGROUND OF THE INVENTION

It is well-known to provide hand tools with a power source. Typically the power source used is electricity, either from batteries or from a mains outlet. However the prior art also discloses the use of alternative power sources for tools and other hand-held implements.

For example, U.S. Pat. No. 6,045,534 discloses an injection device for administering a medicament to a subject, the device being powered by a pyrotechnic charge. WO 01/89612 discloses an injection device powered by an internal combustion engine.

In particular, WO 01/89612 teaches that the fuel/air mixture burnt in the combustion chamber should preferably be compressed prior to combustion. The document discloses in detail one way of effecting such compression, which relies on the user manually to depress a plunger. The document also states that the process "may be effected automatically" but does not disclose any embodiment where compression of the fuel/air mixture is achieved automatically and it is not immediately apparent how this could be done.

The present invention aims to provide a portable device powered by an internal combustion engine in which a fuel/combustion-supporting gas mixture is compressed to a pressure in excess of the ambient atmospheric pressure, and wherein operation of the device is at least partly automated.

SUMMARY OF THE INVENTION

In a first aspect the invention provides a portable powered device such as a tool, comprising a housing within which is defined a combustion chamber for combustion of a mixture of fuel and a combustion-supporting gas, which mixture is compressed so as to be subjected to a pressure in excess of the ambient atmospheric pressure prior to combustion, combustion of the fuel/combination-supporting gas mixture providing the power by which the device performs its intended task, and wherein the said combustion and/or a further combustive event provides the power to compress a successive fuel/combustion-supporting gas mixture, such that a successive cycle of operation of the device may be performed without requiring manual compression of a fuel/combustion-supporting gas mixture by the user.

Preferably the fuel/combustion-supporting gas mixture is pressurised to a pressure of at least 2 bar, more preferably at least 3 bar. Typically the pressure will be in the range 3.5-6 bar.

In a first embodiment a single combustive event provides the power by which the device performs its intended task and also provides (directly or indirectly) the power by which a successive fuel/combustion-supporting gas mixture is compressed for combustion in a subsequent cycle of operation. In an alternative embodiment a first combustive event provides the power by which the device performs its intended task and a further combustive event (e.g. of a smaller dose of the fuel/combustion-supporting gas mixture, which may or may not be compressed prior to combustion) is required to compress a successive charge of fuel/combustion-supporting gas for a subsequent cycle of operation. In such an embodiment the first combustive event will typically occur within a main combustion chamber and the further combustive event will take place in a separate, subsidiary combustion chamber. (Note that the "further" combustive event may actually occur before the "first" combustive event.)

The powered device of the invention is preferably an injection device (needle-less or needle-based) for administering a dose of medicament to a human or animal (typically mammalian) subject. However, the device could be adapted to perform many different tasks or actions currently powered by other means such as motors or compressed air e.g. cutting, drilling, punching, screwing, hammering, spraying, pumping etc. As a specific example, the inventors envisage the device potentially being used as an alternative motive force for otherwise conventional air pistols or air rifles. However, for present purposes the invention will be described in the context of an injector device.

The inventors have envisaged several different methods of achieving at least semi-automation of the device. In the present context "semi-automation" means that one or more steps of the cycle of operation of the device are repeated automatically, in response to one or more actuations of a trigger mechanism, and that at least one step of the cycle which is automated is compression of the fuel/combustion-supporting gas mixture. It should however be noted that an initial cycle of operation may, depending on the embodiment, require specific manual user input—it is the subsequent cycles of operation in which the step is repeated automatically.

Desirably, as well as automatically compressing the fuel/combustion-supporting gas in the combustion chamber, the device will automatically repeat other steps of the operating cycle, such as re-dosing a dose of medicament (in those embodiments in which the device is an injector), automatically operating appropriate vents etc. to admit air or other combustion-supporting gas into the combustion chamber, exhausting combustion products etc.

In a preferred embodiment the device is fully automated (albeit possibly requiring an initial priming action on first use) in that one or more actuations of a trigger mechanism enables the device to perform a complete cycle of operation. If desired, the device could be arranged such that the device will continue to perform cycles of operation whilst the trigger is held, with an interlock mechanism of some kind to ensure that a single cycle of operation is performed only when the device is actually positioned in contact with a subject, and that when removed from contact the operation of the device is interrupted. Whilst at least semi-automation of the device is an important feature of the invention, it will be advantageous to provide a manual override to allow a user to perform a cycle of operation manually (e.g. during an initial cycle for priming, or to purge the device after use or clear blockages or mis-fires etc).

The device will advantageously comprise an interlock or other safety mechanism to reduce the likelihood of accidental discharge and prevent the device from firing unless properly primed. In particular it may be desirable to have a multi-stage actuation or triggering sequence. For example, a trigger mechanism provided on the device may have a plurality of discrete sections of travel, passage therethrough actuating various steps of the operating cycle. Alternatively, the trigger may be depressed fully (or substantially so) a plurality of times, each depression of the trigger causing actuation of different parts of the operating cycle. Yet a further arrangement is for a single actuation of the trigger being sufficient to initiate a cycle of operation, but that various parts of the cycle are subject to delay (by mechanical and/or electrical means) and that one or more sensors can interrupt or prevent parts of the cycle from occurring if conditions are not appropriate (e.g. no medicament in the medicament chamber, or the orifice of the device is not in contact with a subject). The interlock or interrupt mechanism may conveniently be operated by or dependent on input/feedback from the state of the trigger and/or a nozzle guard (e.g. depressed or released).

In one embodiment a combustive event in the combustion chamber acts directly or indirectly on two separately movable pistons: a work piston which, directly or indirectly, performs the work (e.g. expulsion of a dose of medicament from the device); and a priming piston which serves to compress the fuel/combustion-supporting gas mixture prior to combustion, the priming piston being movable between a primed position at one end of its stroke and an exhaust position at the other end of its stroke, and wherein both the work piston and the priming piston are movable in response to the combustive event in the combustion chamber. In one arrangement the work and priming pistons move in opposed directions in response to the combustive event in the combustion chamber. In an alternative arrangement the work and priming pistons move in the same direction in response to a combustive event in the combustion chamber.

In a preferred embodiment, which may preferably be combined with the features described in the preceding paragraph or may be employed separately, there is provided a movable baffle member which communicates with the combustion chamber and forms a gas-tight seal with the inner surface of the housing, the baffle member comprising a one-way valve means which valve means permits entrance of the combustion-supporting gas into the combustion chamber but does not permit egress of combustion products, the baffle member being movable from a first position to a second position in response to a combustive event within the combustion chamber; the device further comprising a return means to return the baffle member from the second position to the first position, which return movement exhausts the combustion products from the combustion chamber. The baffle member may conveniently take the form of a baffle plate and/or be incorporated into the work piston.

The return means may comprise any convenient means of returning the baffle member, such as a spring (especially a constant force spring), a washer, compressed air, or a further combustive event.

Where the device of the invention is an injection device, the device will comprise further operating features which may conveniently be generally as detailed in WO 01/89612, the content of which is specifically incorporated herein by reference.

The combustion-supporting gas may be oxygen or other gas comprising oxygen. Conveniently the combustion-supporting gas will be air.

The device as a whole is typically of such dimensions as to be readily hand-held in use. The barrel needs to be stable at fairly high temperatures and strong enough to withstand the high pressures generated during operation of the device, but is also desirably of low density in order to minimise the weight of the device. The barrel or housing is preferably formed from heat-resistant plastics material or metal (e.g. an aluminium alloy). The device will comprise means for forming a combustible mixture of fuel and air or other combustion-supporting gas in the combustion chamber and will generally comprise a fuel inlet and a separate air inlet. One or both of these inlets may conveniently be provided with valve means to regulate the flow of fuel or air, as the case may be.

The fuel is advantageously one which is gaseous at atmospheric pressure (760 mm Hg) and room temperature (20° C.) but which can be caused to liquefy at room temperature by mildly elevated pressure. Examples of suitable fuels include butane (which is commonly used as a fuel in disposable cigarette lighters) and propane. Desirably therefore the fuel is held as a liquid, under pressure, in a fuel reservoir.

In preferred embodiments of the invention the device provides a substantially consistent power output from one combustive event to the next. In order to achieve this desired objective, it is advantageous to ensure that a consistent amount of fuel is present in the combustion chamber for each combustive event. Accordingly, in preferred embodiments, the device comprises means for introducing an accurately pre-determined amount of fuel into the combustion chamber for each combustive event.

Accordingly, in a preferred embodiment the device of the invention comprises a fuel dosing assembly for metering a dose of fuel from a reservoir of liquefied gas fuel to be delivered to the combustion chamber, wherein the dose of liquefied gas fuel is accurately metered without undergoing a partial phase change. Specifically, in preferred embodiments, the fuel is metered through metering means whilst in the liquid phase, but allowed to vaporize upon expansion on entry into the combustion chamber (typically at atmospheric pressure at this stage of the cycle).

By way of explanation liquefied fuels such as propane and butane tend to vaporize as soon as they are removed from the elevated pressure under which they are stored. The inventors found that this phase change rendered it extremely difficult to meter an accurate dose of fuel consistently. Accordingly, in preferred embodiments it is desired that a liquefied gaseous fuel is measured and dosed whilst still under pressure (and thus in liquid form), which allows for far greater consistency of fuel dosing. Conveniently the fuel dosing assembly comprises a spool valve or a rotary valve, and suitable arrangements are disclosed in WO 01/89612. Alternatively a shuttle valve, of the type employed in pressurised metered dose inhalers, could be employed. The fuel dosing assembly valve or valves may be mechanically or electronically driven.

In preferred embodiments of the device of the invention, the fuel reservoir is pressurised, at a substantially constant pressure, which is effective in keeping all of the fuel in the reservoir in liquid form. Such active pressurizing means may comprise, for example, a spring means acting on a movable pressure plate or piston within the fuel reservoir.

In order to optimise the consistency of power output of the engine, it is desirable that the device will comprise priming means for introducing an accurately pre-determined amount of oxygen, air, or other combustion-supporting gas, into the combustion chamber before each combustive event, or at least ensuring that a large proportion (over 75%, preferably over 85%, more preferably over 95%) of the combustion products are exhausted from the combustion chamber before a successive combustive event occurs, and allowing the exhausted products to be replaced by a corresponding volume of combustion-supporting gas. In particular (but not essentially) it is desirable that the device of the invention includes both a priming means for introducing an accurately pre-determined amount of oxygen or air etc, and a fuel dosing means (as described above) for introducing an accurately pre-determined amount of fuel, into the combustion chamber prior to each combustive event. If desired, a source of combustion-supporting gas may be provided with or incorporated into the device (e.g. a cylinder of compressed air).

For the avoidance of doubt, it should be stated that in some embodiments, the amount of fuel and/or air (or other combustion-supporting gas) introduced into the chamber can be altered between predetermined, fixed amounts. Thus, the power output of the device is consistent for a given volume of fuel and air, but these can be adjusted as desired, to increase or decrease the power output of the device between predetermined set values. Thus, for example, the fuel dosing assembly may be arranged to meter one of several, fixed amounts of fuel. Preferably the fuel and/or air inlets, by which the fuel and air (or other combustion-supporting gas) are respectively introduced into the combustion chamber, will be shaped so as to set up turbulent flow, facilitating mixing of the fuel and air upon entry into the combustion chamber. Forcing fuel and/or air through one-way valve means provided in a baffle plate member is one convenient method of establishing turbulent flow and/or causing thorough mixing.

It will be apparent that in a device in accordance with the invention defined above, in which the combustion chamber is pressurised prior to ignition of the air/fuel mixture, such superatmospheric pressure would tend to displace the piston or pistons communicating with the combustion chamber. In order to resist this the device preferably comprises a restraining means, acting directly or indirectly on the piston/pistons, which serves to keep the piston/s in place against the pressure of the compressed air/fuel mixture, but which is insufficient to restrain the piston when the air/fuel mixture is ignited. In one embodiment the device is provided with one or more spring-biased fingers, typically mounted or acting generally perpendicular to the direction of travel of the piston, which fingers engage co-operatively shaped recesses on the pistons or associated shaft, the spring-biasing acting to urge the fingers into engagement with and thereby restrain, the piston or associated shaft. In an alternative embodiment the restraining member takes the form of a resiliently-deformable, or a rupturable, retaining device. An example of a rupturable retaining device is a shear pin, or similar, which can secure the piston (or work member). In another embodiment the restraining means comprises one or more struts spring-biased, resiliently deformable or deflectable, so as to be displaceable, mounted generally parallel to the direction of travel of the piston, but with an angled surface at the upper end proximal to the piston, the strut or struts being displaceable outwards by the piston upon combustion. Preferably the restraining means automatically re-sets after each cycle of operation—accordingly a shear pin is a less preferred arrangement than a resiliently deformable or deflectable member.

The ignition means conveniently takes the form of a spark plug. This may be powered by a piezoelectric ignition circuit e.g. of the type disclosed in EP 0316468. In preferred embodiments the ignition means will be interlocked such that it is inoperable unless the rest of the device is in a primed state ready to fire. A further preferred feature is that the ignition means can be disabled as soon as combustion has commenced, in order to conserve electrical energy. It may also be desired to limit the electrical output of the ignition means to below the breakdown voltage of the spark gap, and then initiate spark formation in a controlled manner. Controlled ignition may be achieved, for example, by means of a pulse transformer (as used in electronic flash apparatus) or by means of a piezoelectric spark generator, itself insufficient to cause ignition but capable of opening an ionization path for the main spark to follow. Typically the ignition circuit will comprise one or more capacitors and a voltage transducer coil. It is preferred that the spark voltage/power is maintained at a substantially constant value, as this has an effect on the consistency of the combustion in the combustion chamber.

A device in accordance with the invention will generally comprise one or more further components associated with a conventional internal combustion engine. In particular, the device will conveniently comprise at least one exhaust outlet to allow the products of combustion to exit the combustion chamber.

The device may be used to deliver a medicament to a human subject or to any animal subject, including birds (especially poultry), farm livestock (such as sheep, pigs, cattle, goats, horses), and companion animals (especially cats and dogs). It is desirable to minimise the noise of operation of the injection device to avoid discomfort or irritation to the recipient of the medicament, and any nearby people or animals. The inventors have noted that, in this respect, it is desirable that the residual energy of the products of combustion is at least largely dissipated before the exhaust valve is opened, so that venting of the cylinder following combustion is accomplished quietly.

Desirably the exhaust valve or valves are closed throughout the induction, compression, ignition and power delivery phases of the operating sequence and the exhaust valve opens only once the combustion has been completed and all movement (downstroke or upstroke) of the work piston ceased. In one embodiment this is achieved as part of a manual operating sequence, and may typically be the penultimate step of the sequence prior to resetting the piston, ready for storage of the device until it is to be used again. Alternatively, the exhaust valve may be opened automatically (e.g. a determined length of time after ignition). In either event it is preferred that a locking mechanism prevents premature opening of the exhaust valve. Timing and actuation of the valves may be mechanical or electrical.

The device will also further advantageously comprise return means, to return the work piston to a primed position when the device has been fired. The return means may comprise a simple spring biasing means, such as a compression spring which is compressed by the stroke of the piston such that, when the force on the piston from the compressed spring is greater than the force exerted by the gaseous post-combustion products, the piston will tend to return to its primed position (once the exhaust valve or valves have opened). Alternatively, or additionally, the depression of the piston can be used to compress gas in a compartment beneath the piston, thus leading to an increase in pressure acting upwards on the piston which, when it becomes greater than the downward pressure of the combustion products acting on the piston, will tend to return the piston to its primed position. An arrangement incorporating both of these features is disclosed in EP 0 316 468.

The work member typically takes the form of a metallic (e.g. steel) piston rod or push rod welded, screw-threaded or otherwise operably linked with the piston. It should be noted that it is not essential for the work member to be rigidly attached, or physically connected, to the piston. For example, the operable linkage between the piston and the work-member could take the form of a hydraulic fluid-filled conduit, the hydraulic fluid in the conduit serving to transfer energy from the piston to the work member. Additionally or alternatively, one or more solid intermediate members may be disposed between the piston rod and the work member. Such an intermediate solid member may be generally referred to as a "striker". In such an arrangement the piston or piston rod never comes into physical contact with the work member. A preferred arrangement provides a temporary separation (e.g. a small, air-filled gap) between the piston rod and the work member and/or any intermediate striker—the piston initially being separated from the work member or intermediate member when the device is primed, which separation allows the piston to reach a higher velocity (following combustion)

before contacting the work member and/or intermediate member. Accordingly, greater initial acceleration is conferred on the work member than would have occurred if the piston was in physical contact (or otherwise rigidly-linked) with the work member at all times.

It is particularly envisaged that the device of the invention may be used as a means to administer a medicament to animals or to use in mass vaccination/inoculations of human subjects (e.g. in schools, universities, work places or other large institutions).

It will normally be preferred that the device of the invention will perform only a single combustive event when the trigger is actuated so as to avoid, for instance, inadvertent repeated injection of a subject. It will, however, be preferred that the device is provided with sufficient reserves of fuel and (if appropriate) electrical energy that it will be capable of performing a plurality (e.g. a minimum of 1000 or 2000) firing cycles before the fuel and/or electrical energy reserves (if present) are exhausted.

The medicament chamber of the device may contain sufficient medicament for just a single dose for delivery to the subject, so as to require replenishment with medicament after delivery of each dose of medicament. Alternatively, the medicament chamber may contain sufficient medicament for a plurality of doses, such that only occasional replenishment is required. In the latter situation, the medicament chamber will conveniently be provided or associated with dosing means, such that an appropriately-sized, measured dose of medicament is delivered each time the device is used. Desirably the dosing means is adjustable between different positions so that various pre-determined doses of medicament may be delivered.

The medicament chamber may form an integral part of the device of the invention, or may take the form of a readily removable component.

Needleless injectors per se are well known to those skilled in the art. Examples of such devices include those disclosed by Schwebel et al, which are powered by a pyrotechnic charge (see U.S. Pat. No. 3,802,430; U.S. Pat. No. 4,089,334 and U.S. Pat. No. 4,124,024).

It is desirable that devices such as needleless injectors have a consistent power output: whilst, on one hand, sufficient power must be provided to force the medicament or other substance through the skin, it is necessary to avoid the use of too much power, otherwise the substance may be injected deeper than is required and may cause greater disruption to the tissues (especially blood vessels) of the subject than is required, leading to extensive and unsightly bruising, and cause pain.

Those skilled in the art will be acquainted with the types and doses of substances which are deliverable by a needleless injector. A typical dose volume will be between 0.01 ml and 2.0 ml. The substance to be delivered may take the form of a liquid (a solution or suspension), but other formulations may be employed.

Ideally, in order to reduce or minimise sensation of pain associated with the injection, the medicament should be administered within an injection interval of less than 500 milliseconds, preferably about 200 milliseconds. Further, in an ideal embodiments, there is an initial peak in the injection force provided by the injector in order to overcome the resistance provided by the subject's skin, followed by a longer, sustained force of lower magnitude to deliver the medicament dose. The initial penetrating force is typically in the range 0.4-1.4 Newtons, and the medicament delivery force is advantageously in the range 0.2-0.8 Newtons.

An injection device orifice, through which the medicament is expelled, will conveniently have a diameter in the range 0.1-0.5 mm, more preferably in the range 0.12-0.45 mm. An orifice of these dimensions, with average forces of the magnitude described above, would create an initial medicament velocity of about 120 m/s to penetrate the skin, with the rest of the medicament dose being delivered at a velocity of about 70 m/s. A preferred velocity is in the range 50-150 m/s, which is found suitable for transdermal delivery of most or all of an average dose of medicament to a typical human subject.

In a second aspect the invention provides a portable tool which performs a cyclical operation, typically an injector device, comprising a multi-component work member assembly, which components after performance of one cycle of operation are automatically returned to their starting positions ready for performance of another cycle. Desirably the tool of the second aspect of the invention will be generally in accordance with the tool of the first aspect defined above.

In particular, the work member assembly will typically comprise a work piston rod or similar, an intermediate striker member and an end work member (such as a plunger). Typically the work piston rod and the intermediate member will be co-axially mounted, conveniently on a common guide means such as a shaft or linkage, which may typically pass through a central bore provided in both the work piston rod and the intermediate member.

Advantageously the components of the work assembly are such that, at the start of the cycle the intermediate member is in spaced apart relationship with the end member and also with the work piston rod. During operation of the device, the work piston accelerates over the central shaft moving relative thereto. After a short period of travel the end of the work piston rod contacts the intermediate member, and the two latter components move together, relative to the central shaft, until they contact the end member, forcing the end member to perform the desired end task (e.g. expulsion of a medicament from a chamber). After reaching the end of its stroke, the work piston rod commences its return stroke under the influence of a return means. However the work piston rod does not immediately engage the central shaft, so that a spaced apart relationship with the intermediate member is re-established.

In a convenient embodiment the intermediate member comprises a paramagnetic or, more preferably, ferromagnetic material, and a permanent magnet or electromagnet provided on or in the device applies a weak magnetic force sufficient to compel the intermediate member to take up a position between the end member and the work piston rod in spaced apart relationship therefrom.

In a further aspect the invention provides a method of administering a medicament to a human or animal subject, the method comprising use of an injector device in accordance with the first or second aspects of the invention defined above.

BRIEF DESCRIPTION OF THE DRAWINGS

The invention will now be further described by way of illustrative example and with reference to the accompanying drawings, in which:

FIGS. 1 and 2a are longitudinal sections of an injector device in accordance with the invention, the section of FIG. 2a being at 90° to the section of FIG. 1;

FIG. 2b illustrates one example of an exhaust valve means for incorporation in the device of the invention.

DETAILED DESCRIPTION OF EMBODIMENTS

Figure 1:
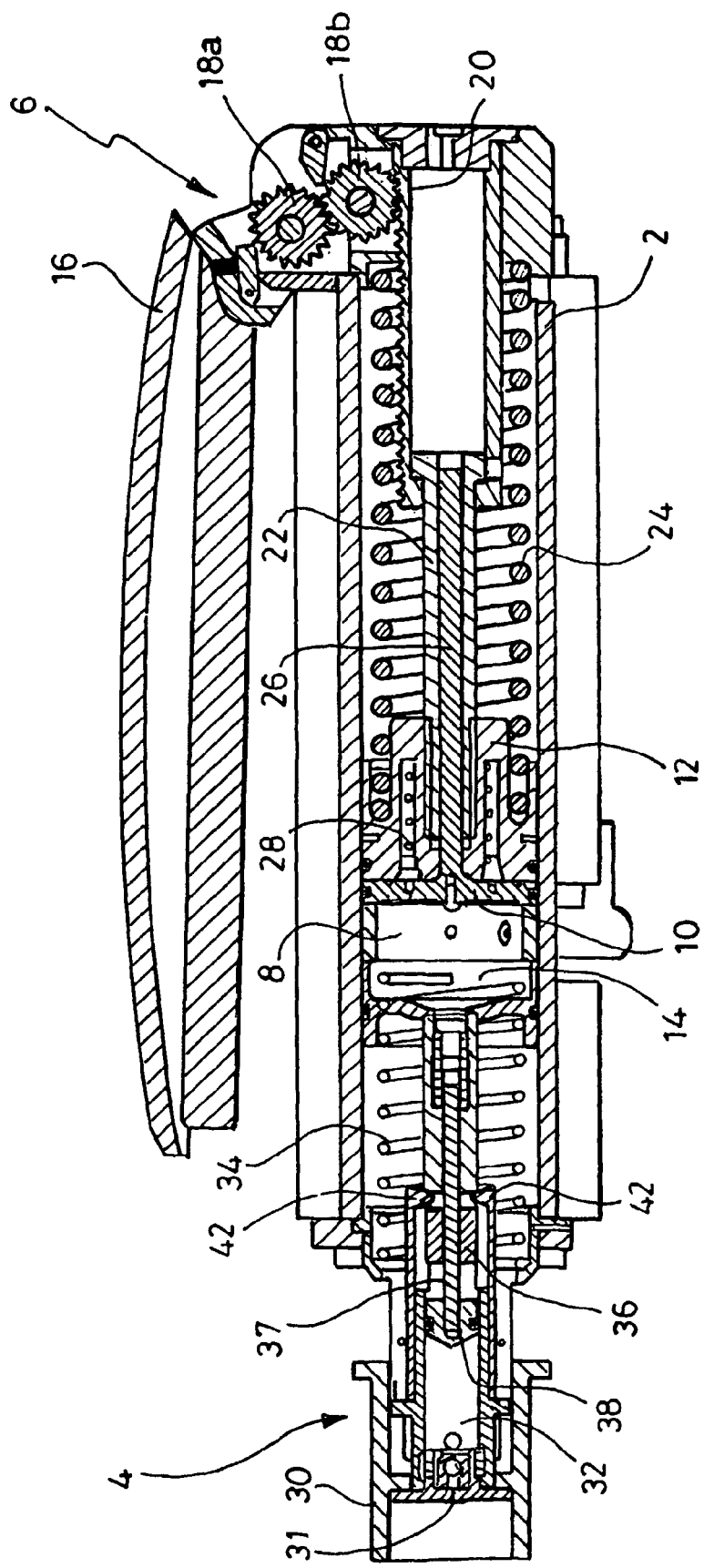

A first embodiment of a device in accordance with the invention takes the form of a needle-less injector for administering a dose of medicament to a human or animal subject, and is depicted in longitudinal sectional view in FIGS. 1 and 2a.

Referring to those Figures, the injector comprises a housing in the form of generally cylindrical barrel 2, formed from aluminium. Disposed towards one end of the barrel 2 is a nozzle assembly indicated generally by reference numeral 4 and disposed towards the opposite end of the barrel 2 is a priming assembly indicated generally by reference numeral 6. Within the barrel 2 is a combustion chamber 8 defined at one end by a baffle plate 10 associated with a priming piston 12, and defined at the other end by a work piston 14. When the device is primed, a combustible mixture of fuel/combustion-supporting gas is held within the combustion chamber 8, at a pressure in excess of ambient atmospheric pressure.

The device also includes (shown in varying degrees of detail) an ignition means for igniting the combustible mixture in the combustion chamber, a trigger mechanism for actuating the ignition means (and optionally actuating other components of the device also), an exhaust system for venting the products of combustion from the combustion chamber 8, fuel and air inlet means for introducing fuel and air or other combustion-supporting gas into the combustion chamber 8.

The various components of the device and its operation will now be described in more detail. The embodiment depicted in FIGS. 1 and 2a is appropriate for the delivery of a 2 ml dose of medicament, using jet pressures (at the nozzle of the instrument) in excess of 300 bar. The inner bore of the barrel 2 is 36 mm in diameter, and the overall length of the complete device is about 300 mm.

The priming assembly 6 comprises a lever 16 (for initial manual priming of the device), associated gear wheels 18a, b, one of which (18b) engages with a ratchet surface of a priming tube 20. Inside the priming tube 20 is a priming shaft 22, mounted at one end of which is the priming piston 12. A priming spring 24 is seated within an annular recess on the rear face of the priming piston 12 and extends, within the barrel 2 towards the rearmost end of the barrel. In general terms, the "front" end of the device may be considered as the end region comprising the nozzle assembly, and the "rear" end may be considered as the end region comprising the gear wheels 18a,b.

Associated with the priming assembly is the baffle plate 10 and a baffle piston 26. The baffle plate 10 is a circular flange mounted at one end of the baffle piston 26 which is itself located within a circular bore provided in the priming shaft 22. A baffle spring 28 is located between the rear face of baffle plate 10 and the front face of the priming piston 12. A deep annular recess is provided in the priming piston 12 to accommodate the baffle spring 28. The baffle spring 28 acts to urge the baffle plate 10 towards the combustion chamber 8. A gas-tight seal is provided between the edge of the baffle plate 10 and the inner surface of the barrel 2. The baffle plate 10 is provided with one-way valve means which permits entrance of combustion-supporting gas (in this instance, air) into the combustion chamber 8 but does not permit the egress of combustion products. In the embodiment illustrated the one-way valve means comprises a plurality of 2 mm diameter valve holes drilled through the baffle plate 10, which holes are covered by a thin, stainless steel valve plate. The valve plate can lift off the baffle plate 10 in response to a positive pressure differential to the rear of the baffle plate 10, allowing combustion-supporting gas to enter the combustion chamber 8. In contrast, a positive pressure differential inside the combustion chamber 8 forces the valve plate against the baffle plate 10, closing the valve holes, preventing egress of combustion products from the combustion chamber 8.

The baffle plate 10 and baffle piston 26 are movable relative to the priming piston 12 and priming shaft 22.

The nozzle assembly 4 comprises a nozzle guard 30, a dosing chamber 32 to contain a dose of medicament to be injected, the work piston 14, a work piston spring 34 seated between the work piston 14 and the front end of barrel 2, and an orifice or nozzle 31.

Actuation of the device causes the work piston 14 to move forward at high velocity, so as to encounter striker 36. This in turn accelerates the striker 36 to act on plunger 38, forward movement of which expels the dose of medicament from the dosing chamber 32 through orifice 31 and into the subject.

As explained above, the fuel/combustion-supporting gas mixture in the combustion chamber 8 is pressurised in excess of ambient atmospheric pressure prior to combustion. Accordingly it is necessary to provide retention means to act so as to keep the baffle plate 10 and/or the work piston 14 (preferably both) in place, against the excess pressure in the combustion chamber 8, when the device is in the primed condition. In one arrangement a single retention means may be provided to act (directly or indirectly) on both the baffle plate 10 and the work piston 14. In an alternative arrangement, a separate retention means is provided to act on the respective components mentioned above. In the embodiment illustrated in FIGS. 1 and 2a, a trigger/latch mechanism (denoted generally by reference numeral 40 in FIG. 2a) is provided which (together with the action of priming spring 24), indirectly, acts to retain the baffle plate 10 in place when the device is primed; and the work piston 14 is retained partly by the action of work piston spring 34 but primarily by deflectable metal struts, two of which (42) are shown in FIG. 1.

The operation of the device as a whole, and of particular components therein, will now be described in detail.

Upon first use of the device, a manual priming operation must be performed for the initial cycle, in order to generate the pressurised mixture of fuel/combustion-supporting gas in the combustion chamber 8. In the embodiment shown in FIGS. 1 to 3 the combustion-supporting gas is air.

Referring to FIG. 1, operation of the priming lever 16 drives a train of gear wheels 18a,b which in turn draw back the priming tube 20 out of the rear of the barrel housing. The priming tube 20 in turn retracts the priming shaft and priming piston 12 to a point where an accommodating recess on the priming piston 12 enters into a snap fit engagement with the latch of trigger latch mechanism 40 and is retained. The priming tube 20 is then pushed back inside the barrel 2, where it is positioned during subsequent operation of the device.

It is advantageous, to simplify operation, that the forces involved in priming the device are not too high. Accordingly, it may be beneficial to allow air to enter during the retraction of the priming piston 12, otherwise the manual priming must do work in creating a partial vacuum between the piston 12 and the baffle plate 10. A number of ways can be envisaged to allow air to enter the combustion chamber 8 in a controlled manner e.g. allowing air to flow forwards into the combustion chamber past the seal provided around the priming piston 12 in a one-way manner, or to incorporate a check valve in the baffle plate 10, such that a limited flow of air can pass backwards across the baffle plate for low pressure differentials (i.e. not during combustion). Yet another approach might be to allow one or more exhaust ports to be open during priming, allowing air into the combustion chamber 8 such that the baffle plate 10 can move backwards with the priming position 12—the baffle spring 28 would then act to return the baffle plate 10 to its desired position.

The space vacated by the retraction of the priming piston 12 is filled with air at atmospheric pressure, and the exhaust port or ports of the device are closed. On an initial partial actuation of the trigger mechanism 40 (shown in FIG. 2a), fuel for the combustion process—typically butane but potentially also other appropriate fuels such as propane, or a mixture of such fuels—is introduced into the combustion chamber 8. In the current embodiment this is via the release and expansion into the chamber 8 of fuel held under pressure in the liquid phase. In an alternative arrangement fuel is introduced into the volume behind the baffle plate 10 and forced therethrough into the combustion chamber 8, thereby aiding mixing.

On further depression of the trigger, the trigger mechanism 40 releases the trigger latch which in turn releases the priming piston 12. This is driven towards the baffle plate 10 through the action of a compressive component or components—in this case the priming spring 24—and in the process it forces the air in front of it through the baffle plate 10 non-return valve into the combustion chamber 8. (Seals prevent the flow of air between the priming piston 12 and the baffle piston 26, and between priming piston 12 and the inner surface of the barrel 2.) Because of the pressures and contact forces involved and the desire to keep the device as small as practically possible, it may be advantageous for the trigger mechanism to give mechanical advantage such that the actuation force is not too high. This can be achieved in a number of ways, such as through the inclusion of linkages and/or levers.

As the priming piston 12 is pushed to its forwardmost position, contacting the back face of the baffle plate 10, the pressure in the combustion chamber rises to a specific predetermined value. This can be controlled through selection of the appropriate travel geometries and combustion chamber volume, and is typically of the order of 2-6 bar for the configuration described. The work piston 14 is secured in place against the combustion chamber 8 during this action by a combination of the work piston spring 34 and an additional re-settable release mechanism which, in the embodiment depicted, takes the form of two deflecting metal release struts 42 which deflect to release the piston once a given load threshold is reached and return to the engaged position as the piston returns. Further depression of the trigger culminates in an action (in this instance, the closing of a switch in an electrical circuit) which generates a spark via one or more spark plugs which protrude into the combustion chamber 8. Given a spark of sufficient power and voltage, generated by an ignition circuit incorporated within the device, ignition of the pressurised fuel/air mixture occurs, leading to rapid combustion.

As combustion occurs, pressure within combustion chamber 8 rises rapidly. This results in an increase in the forward force on the work piston 14 but the piston is prevented from moving any significant distance forward by the release struts until the pressure reaches a target value. At this point the struts 42 deflect, releasing the work piston 14 which then moves forward rapidly under the increasing pressure of combustion.

The combustion process also causes re-setting of the priming system. In the illustrated embodiment, the expanding gases are prevented from passing back through the holes in the baffles plate 10 by the non-return valve means. Hence the pressure drives the baffle plate 10 and priming piston 12 back towards the rear of the device, against the resistive forces of the priming spring 24 (and, if appropriate, a second release mechanism). The baffle plate 10 and priming piston 12 are pushed backwards to the point where the priming piston passes the trigger latch(es) which deflects and then springs back so as to secure the piston 12 in the primed position. Note that the mechanism must be such that this occurs even if the trigger is still being held in the 'fire' position. In this location, a priming piston seal now lies just behind small air inlet apertures (denoted by reference numeral 11) in the barrel 2 (shown in FIG. 2a, immediately in front of the latch) which hence allow the entrance of the air charge for the next operation sequence.

The baffle plate 10 however is not latched in place and is pushed back towards the combustion chamber 8 by the baffle spring 28. In so doing, the baffle plate 10 tends to compress the combustion products retained within the sealed combustion chamber. Combustion products are also compressed by the work piston 14 which begins its return towards its home position, urged by the work piston spring 34.

The combustion products are exhausted and the baffle plate 10 and work piston 14 return fully to their home positions when the exhaust port (not shown) is opened. This can occur as soon as the full forward action of the work piston 14 and plunger 38 and the re-priming action of the priming piston 12 have taken place, and may be time accordingly. One way of achieving this is to link the state of the exhaust port to the position of the sprung nozzle guard 30 which is maintained in the extended position until just before firing when the action of the operator pushes the guard into a retracted position by applying a force against the subject. When the nozzle guard 30 is depressed, the exhaust valve is closed and combustion can take place, but when the guard 30 is released (just after firing) by removing the nozzle guard 30 from contact with the subject the exhaust port returns to its normally open state, allowing expulsion of combustion products from the chamber 8 by the returning priming and work pistons 12, 14 respectively.

FIG. 2b illustrates one possible exhaust port configuration, where an exhaust block 50 is provided with a guide tube 52. Running axially within guide tube 52 is a shaft 54 which drives an exhaust valve shuttle 56 against a spring 58. Two seals 60 prevent flow of gases between the valve shuttle 56 and the inner bore of exhaust block 50 and guide tube 52.

The assembly shown is fixed on the side of the main barrel 2 with a port 62 connecting the combustion chamber 8 to the open bore in the exhaust block. The normally open exit route from this bore is via a bore through the valve shuttle 56 and out through a side port (not shown). When the nozzle guard 30 is depressed, a linkage to the shaft 54 forces the valve shuttle 56 to move into the block 50, compressing the spring 58 and moving the innermost seal 60 beyond the exhaust exit bore which now lies between the two seals, thus closing the exit route for any gases in the chamber 8. When the nozzle guard 30 is released, the spring 58 (potentially in conjunction with a further spring on the guard itself) returns the shaft 54 and valve shuttle 56 to the normal position, opening the valve. In other configurations the exhaust port state could be linked to other parameters such as trigger positioning or timing circuits.

The work piston and other 'dose delivery' components are also self-positioning as part of the re-priming process. For a single work piston/plunger component this is readily accomplished as the return of the work piston will automatically re-position the plunger to which it is fixed. For configurations, such as that illustrated in FIGS. 1 and 2a, in which energy from the combustion event in combustion chamber 8 is transmitted to the dosing chamber 32 by a train of components, automatic self-positioning is more complicated.

In the embodiment shown, self-positioning of the dosing assembly is achieved by having the plunger 38 connected to the work piston 14 via a rigid linkage 37 which runs freely through the center of the work piston 14 and also the striker 36. When, during combustion the work piston 14 accelerates forward initially, it passes freely over the linkage 37 and hence plunger 38 and striker 36 do not move. It is only when the front face of the work piston 14 strikes the back face of the striker 36 that these components begin to move forward, separately at first but then coalescing together to form a single unit. The combined work piston 14/striker 36 then impact on the rear face of plunger 38, pushing it through the dosing chamber 32 and thereby expelling a dose of medicament. On its return the work piston 14 does not pick up the linkage 37 immediately and hence the gap between piston 14 and plunger 38 and striker 36 is re-established. The striker 36 is pushed or pulled into position in between the piston 14 and plunger 38 by an externally applied force e.g. from one or more magnets housed in the dose chamber 32.

Refilling of the dose chamber 32 also takes place automatically. When the work piston 14 pulls the plunger 38 back, a check valve in the nozzle prevents air being drawn in through the orifice. The resulting suction instead draws a new dose of medicament through a feed line from a dose reservoir (either a bottle, held within the device, or a hose line to separate tank). A check valve in this feed line close to the dose chamber inlet prevents back flow of dose during actuation.

Figure 3A:
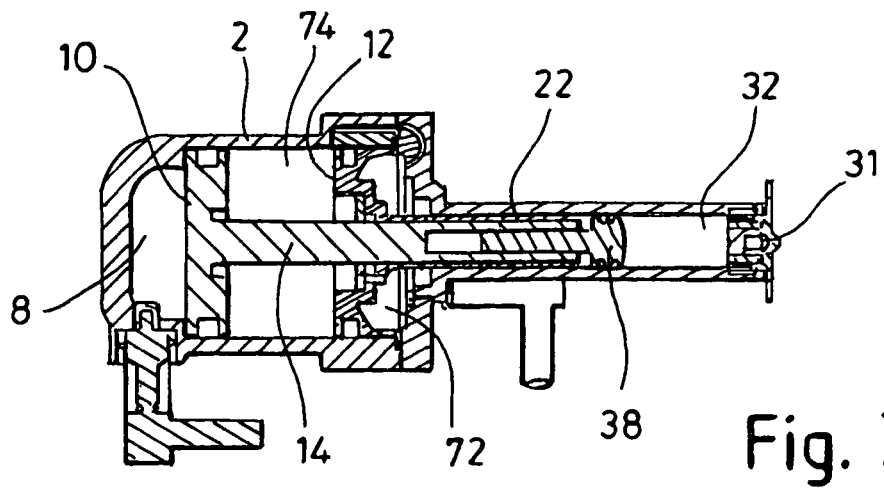
FIGS. 3a-c are a series of longitudinal sections of a different embodiment of an injector device in accordance with the invention, showing three stages, a, b and c respectively, in the operation of the device.
Figure 3B:
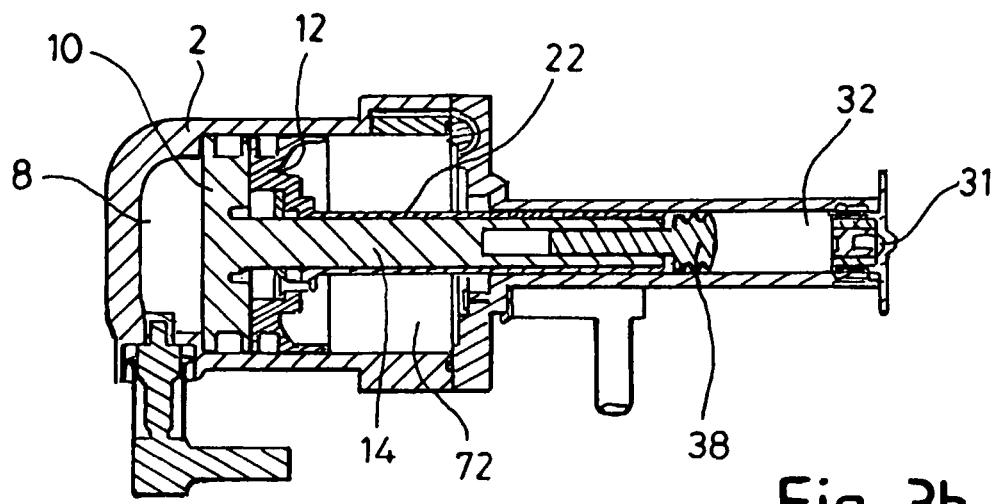
Figure 3C:
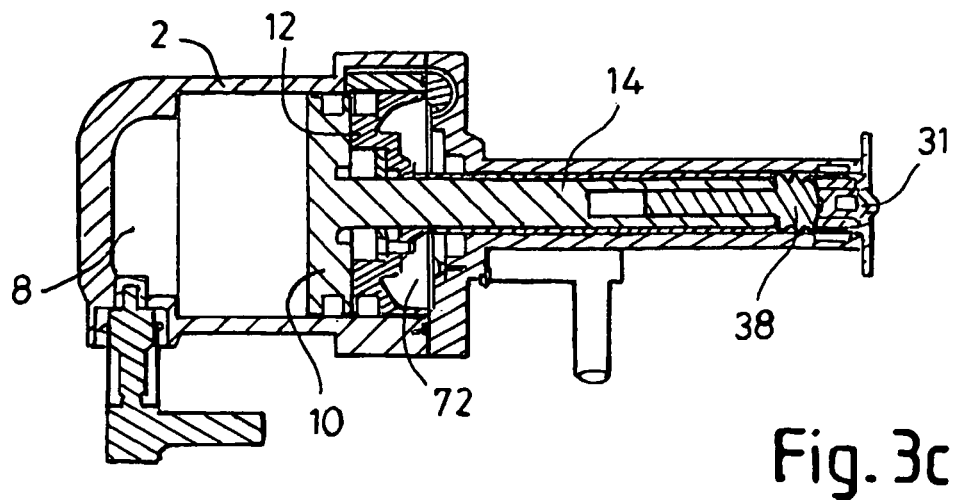

A different embodiment of the invention is shown in FIGS. 3a-c. The embodiment employs many of the general features of the embodiment shown in FIGS. 1 and 2a, i.e. an injector device in which an internal combustion engine is used to provide the motive force to expel a dose of medicament through an orifice into a subject and wherein the device comprises both a work piston 14 and a baffle plate 10. Thus, where components are functionally equivalent to those illustrated in FIGS. 1 and 2a the same reference numerals are employed.

Referring to FIG. 3, an injector device comprises a generally cylindrical housing in the form of a barrel 2, within which is provided a priming piston 12 mounted on a priming piston shaft 22, and a baffle plate 10, which are movable relative to one another. The baffle plate 10 is mounted on a work piston 14 which is received within a central bore provided within the priming piston shaft 22.

As in the previously described embodiment, the priming piston 12 and baffle plate 10 are provided with appropriate sealing means to form a gas tight seal with the surfaces over which they move, and baffle plate 10 is additionally provided with one-way valve means which permits entrance of a combustion-supporting gas (in this instance, air) into the main combustion chamber 8, but which does not permit the egress of combustion products. The main combustion chamber 8 is defined at one end by the surface of baffle plate 10 and at the other end and sides by the barrel 2. The device also comprises a subsidiary combustion chamber 72. Both the main and subsidiary combustion chambers 8, 72 are provided with a respective spark plug. The subsidiary combustion chamber 72 is at the opposite end of the barrel to the main chamber 8, and is defined by the surface of priming piston 12 at one end region and at the opposed end region by the barrel 2.

FIGS. 3a-c show sequential stages in operation of the device. In FIG. 3a the device has been fired and the priming piston 12 has reached the end of its stroke; the baffle plate 10 and plunger 38 have returned to the positions they assumed prior to firing. In the case of the baffle plate 10, the return is mediated by a return means in the form of a baffle plate spring (not shown) provided between the rear face of the baffle plate 10 and the front face of the priming piston 12. All the valves are closed, there is a dose of medicament in the dosing chamber 32 and there is air at atmospheric pressure in both main and subsidiary combustion chambers 8, 72 and in the volume 74 between the baffle plate 10 and priming piston 12.

Liquid fuel is then metered into the device where it evaporates to become gaseous. This can either be done by having two separate fuel reservoirs and metering valves operated simultaneously or, more preferably, through a single reservoir and metering valve whereby the total amount of fuel required is metered into a feed chamber and then released into the device such that the chambers 8, 72 fill to equal pressure. Relative volumes of the main and subsidiary combustion chambers will ensure that the correct amount of fuel is introduced into the two chambers 8, 72. The fuel may be metered directly into the respective combustion chambers 8, 72, or may be metered into the device and then indirectly introduced into the combustion chambers. In a preferred arrangement, fuel for the combustion chamber 72 is metered directly into the chamber, whilst fuel for chamber 8 is metered into the volume 74 and then forced through valve means in baffle plate 10 into the chamber 8, which arrangement facilitates mixing of the fuel and air.

The subsidiary combustion chamber 72 now contains a gaseous mixture of fuel and air at atmospheric pressure (FIG. 3a). On sparking of the corresponding spark plug this mixture is ignited and combustion occurs. This results in rapid expansion of the gases in the chamber 72 which drives the priming piston 12 backwards towards the baffle plate 10, compressing the baffle plate spring (not shown) and forcing the air through the one way valve(s) in baffle plate 10 into the main combustion chamber 8. Seals on the mating shafts prevent the compressed air passing between the baffle plate 10 and the priming piston 10. Seals on the outer diameters prevent flow of air between priming piston 12 and/or baffle plate 10 and the barrel 2. The main combustion chamber 8 now contains a pressurised gaseous fuel/air mixture which may be at pressures typically between 2 and 6 bar (FIG. 3b), so that the device is primed.

On sparking of the second spark plug, the timing of which can be governed by the ignition circuit employed, combustion takes place in the main combustion chamber 8, and the combination of baffle plate 10/work piston 14 and priming piston 12 are driven rapidly forwards. Simultaneously, or very shortly afterwards, a valve (or valves) on the subsidiary combustion chamber 72 is opened and this allows the combustion products in the subsidiary combustion chamber 72 to be exhausted, preventing the build up of retarding forces on the priming piston 12. The operation and timing of this valve may be mechanical or electrical e.g. through the use of a solenoid valve driven from the main ignition circuit. As the baffle plate 10 moves forward, the linkages between it and the plunger 38 result in an amount of lost motion followed by rapid forward motion of the plunger 38. In the case of the injector application shown, this would result in the dose of medicament being expelled from the chamber 32, but in other applications it could have other results e.g. the generation of a volume of compressed air. The stage finishes when baffle plate 10 and work piston 14 are pushed forward against the end wall of the barrel 2 and the plunger 38 is at the end of its travel in the dosing chamber 32 (FIG. 3c), and the priming piston 12 is at the end of its stroke abutting one end region of the barrel 2.

As shown, this embodiment does not include retaining struts to prevent forward movement of the work piston 14 until a threshold pressure is reached, or a striker to improve the pressure delivery profile. Such struts (or other motion limiting/release mechanism) or striker components could of course be incorporated if required.

An exhaust valve on the main combustion chamber 8 is now opened, again either on a mechanical link from direct or indirect user input or on an electrical signal from the main ignition circuit to a solenoid valve. With the valve open the baffle plate 10 is pushed away from the priming piston 12 by the baffle plate spring, resulting in exhaustion of the combustion gases from the main chamber.

In order to permit free forward travel of the baffle plate 10, and also so as to prepare for the next operation cycle, air needs to drawn into the system. For the embodiment shown, this is achieved through an open passage that runs from a point in the front wall of the subsidiary combustion chamber 72 to a point in the barrel wall just in front of the baffle plate 10. As the baffle plate is pushed backwards, air is drawn via the subsidiary combustion chamber 72 and its open exhaust port into the space just behind the baffle plate, in the process also replacing any remaining combustion gases in the main combustion chamber 8 with new air. Once any lost motion has been taken up, the return travel of the baffle plate 10/work piston 14 also pulls the plunger 38 back to its starting position.

Once the baffle plate 10 has returned to its starting position, both exhaust valves are closed and the system is ready to repeat the firing sequence.

It is noted that initial manual priming of this embodiment is not required as there is no compression of the gas in the subsidiary combustion chamber.

The major differences between the embodiment shown in FIGS. 1 and 2a and that depicted in FIGS. 3a-c are:
  a) the main combustion chamber 8 is disposed towards one end of the barrel 2 in the second embodiment, and accordingly both baffle plate 10 (and work piston 14 on which the baffle plate is mounted), positioned to one side of the chamber 8, move in the same direction in response to a combustive event in the chamber, whereas in the first detailed embodiment the combustion chamber 8 is more centrally positioned within the device with the baffle plate 10 and work piston 14 positioned on opposite sides of the combustion chamber with the result that a combustive event in the chamber 8 forces the baffle plate 10 and work piston 14 apart, in opposite directions.
  b) The second main difference is the provision of a subsidiary combustion chamber, wherein a combustive event taking place in the subsidiary chamber provides the motive force for achieving priming of the fuel/air mix in the main combustion chamber.
  c) Another difference, implicit in the description above, is that in the embodiment illustrated in FIG. 3, the baffle plate 10 is mounted on the work piston 14, whilst in the embodiment shown in FIGS. 1 and 2a, the baffle plate 10 is mounted on an additional baffle plate piston, the work piston 14 being separate.

The arrangement shown in FIGS. 3a-c has an advantage relative to that shown in FIGS. 1 and 2a, in that the work piston 14 performs the dual role of both transmitting energy from the combustion chamber 8 to the dosing chamber 32 on the "down" stroke and, on its return stroke, primes the fuel/air mix in the combustion chamber 8 for the next cycle of operation. This arrangement avoids the need for a priming spring and other bulky components, with the overall result that the device can be made much more compact than the arrangement shown in FIGS. 1 and 2a.

Another advantage of the second embodiment, as already noted, is that an initial manual priming of the device is not required. Yet further advantages are that the trigger latch is no longer required to withstand a large force (from a powerful priming spring) and that substantially all of the energy of the combustion from the main combustive event (in chamber 8) can be used for the desired output without any energy being diverted to re-priming of the device.

The invention claimed is:

1. A portable powered device, comprising:
a housing;
a main combustion chamber within the housing for combustion of a mixture of a fuel and a combustion-supporting gas, the combustion chamber being defined by the housing and by a baffle plate;
a priming piston in the housing on a side of the baffle plate opposite the main combustion chamber to compress the mixture of a fuel and a combustion-supporting gas to a pressure in excess of ambient atmospheric pressure prior to combustion;
a subsidiary combustion chamber within the housing for combustion of a second mixture of a fuel and a combustion-supporting gas, the subsidiary combustion chamber being defined by the priming piston;
a work piston, extending from the baffle plate, which performs the work required of the device;
the work piston and the priming piston being separately movable in response, directly or indirectly, to combustion of the mixture of the fuel and combustion-supporting gas in the main combustion chamber and the subsidiary combustion chamber;
and whereby energy released by combustion of the fuel and the combustion-supporting gas in the subsidiary combustion chamber is used to compress a mixture of the fuel and combustion-supporting gas in the main combustion chamber to ready the device for displacement of the work piston.

2. A device according to claim 1, wherein the movable baffle plate forms a gas-tight seal with an inner surface of the housing, the baffle plate comprising a one-way valve means which valve means permits entrance of the combustion-supporting gas into the combustion chamber but does not permit egress of combustion products, the baffle plate being movable from a first position to a second position in response to a combustive event within the combustion chamber; the device further comprising a return means to return the baffle plate from the second position to the first position, which return movement exhausts the combustion products from the combustion chamber.

3. A device according to claim 1, wherein a combustive event within the main combustion chamber provides the power by which the device performs its intended task and a further combustive event within the subsidiary combustion chamber provides, directly or indirectly, the power by which a successive fuel/combustion-supporting gas mixture is compressed for combustion in a subsequent cycle of operation.

4. A device according to claim 3, wherein the main and subsidiary combustion chambers are disposed towards opposed end regions of the housing.

5. A device according to claim 1, wherein the work piston and priming piston move in the same direction in response to a combustive event in the main combustion chamber.

6. A device in accordance with claim 1 including means for dispensing doses of a liquid.

7. A device according to claim 1 including means for administering a dose of medicament to a human or animal subject.

8. A device according to claim 1, comprising a multi-component work member assembly, which components after performance of one cycle of operation are automatically returned to their starting positions ready for performance of another cycle.

* * * * *